(12) United States Patent
Ohno et al.

(10) Patent No.: US 6,248,357 B1
(45) Date of Patent: Jun. 19, 2001

(54) SOLID PHARMACEUTICAL PREPARATION WITH IMPROVED BUCCAL DISINTEGRABILITY AND/OR DISSOLUBILITY

(75) Inventors: Yasuo Ohno, Osaka; Tadashi Makino; Junichi Kikuta, both of Ibaraki, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/351,253

(22) Filed: Jul. 12, 1999

Related U.S. Application Data

(62) Division of application No. 08/960,353, filed on Oct. 29, 1997, now Pat. No. 5,958,453.

(30) Foreign Application Priority Data

Oct. 31, 1996 (JP) .................................................. 8-290606

(51) Int. Cl.⁷ ............................. A61K 9/20; A61K 47/30; A61K 47/26
(52) U.S. Cl. ...................... 424/465; 514/772.5; 514/781; 514/960
(58) Field of Search ............................ 424/465; 514/960, 514/772.5, 781

(56) References Cited

U.S. PATENT DOCUMENTS 4,371,516  2/1983  Gregory et al. ....................... 424/22
5,958,453 * 9/1999  Ohno et al. .......................... 424/465

FOREIGN PATENT DOCUMENTS

| 0 336 298 | 10/1989 | (EP) . |
| 0 345 787 A2 | 12/1989 | (EP) . |
| 0 365 480 A1 | 4/1990 | (EP) . |
| 0 438 147 A2 | 7/1991 | (EP) . |
| 0 553 777 A2 | 8/1993 | (EP) . |
| 0 638 310 A2 | 2/1995 | (EP) . |
| 0 745 382 A1 | 12/1996 | (EP) . |
| 92/11001 | 7/1992 | (WO) . |

OTHER PUBLICATIONS

Derwent Abstract of JP Patent No. 9048726.
Abstract No. 97–231144/21 of JP 09071523A.
Abstract No. 89–359871 of JP 1268627A.
Abstract No. 89–359872/49 of JP 1268628A.
Abstract No. 136212/14 of JP 08027033A.
Derwent Abstract 98–110347 of WO/02185 to Daiichi Pharmaceutical and English translation of claims.

\* cited by examiner

*Primary Examiner*—Carlos A. Azpuru
(74) *Attorney, Agent, or Firm*—Wenderoth, Lind & Ponack, L.L.P.

(57) ABSTRACT

A solid pharmaceutical preparation comprising a pharmaceutically active ingredient, erythritol, crystalline cellulose and an disintegrants, which exhibits a fast buccal disintegratability and dissolubility.

16 Claims, No Drawings

SOLID PHARMACEUTICAL PREPARATION WITH IMPROVED BUCCAL DISINTEGRABILITY AND/OR DISSOLUBILITY

This application is a divisional of Ser. No. 08/960,353, filed Oct. 29, 1997, now allowed as U.S. Pat. No. 5,958,453.

BACKGROUND OF THE INVENTION

1. Field of the Invention

The present invention relates to a solid pharmaceutical preparation, especially a buccal dissolution type solid preparation having characteristics of fast disintegration or dissolution in the oral cavity even without water.

2. Description of Related Art

Generally, solid pharmaceutical preparations such as tablets are designed so that after they are orally administered, they disintegrate or dissolve in the digestive organs and the pharmaceutically active ingredients are absorbed. Accordingly, fast disintegration or dissolution in the oral cavity is not a common design feature.

However, in accordance with the increase in the aged population and change in life styles, there has been a need for development of buccal dissolution type solid preparations which can be, if necessary, administered readily even without water, by aged people and children anywhere or anytime, maintaining the convenience typically afforded by pharmaceutical tablets.

As the technique for producing preparations which quickly disintegrate or dissolve in the oral cavity, heretofore, there has been proposed a method for producing preparations by dissolving or suspending pharmaceutical or medicinal ingredients in an aqueous solvent, filling the resultant solution or suspension into a pocket molded beforehand in a blisterpack and reducing water content from the solution by freeze-drying or vacuum drying [USP 4371516 (Examined Japanese Patent Application Publication (Kokoku) No. 62(1987)-50445), (W/O 93/12769) (Publication of Translations of International Patent Application. No. 5-812769)]. This method, however, has problems in that it takes time for manufacturing and in that the obtained products have insufficient strength and thus are difficult to handle. There is known another method in which a mixture of a pharmaceutically active ingredient with a low moldability saccharide is granulated with a high moldability saccharide added thereto [EPA 745382, (Publication of Translations of International Patent Application No. 7-820380 (WO 95/20380))]. The product obtained by this method has such hardness that the dosage form remains without being disintegrated in the course of distribution, while the method has a problem that tabletting is not easy, as is often the case with high moldability saccharides, because tabletting is carried out with lower pressure. Also the products have an additional defect that they leave a problem to be solved in terms of buccal fast disintegration and dissolution. On the other hand, have been made of buccal dissolution preparations produced by wetting molding. But, in general, tablets having fast disintegration or dissolution have defects of lack in strength.

From the foregoing view-point, there is a need or demand for development of preparations which exhibit excellent buccal disintegration and dissolution and also an appropriate strength such that the preparations never disintegrate or suffer damage in the course of the production steps or distribution stages. Japanese Patent Applications Laid-open Nos. 1-268627, 1-268628 and 8-27033 describe a pharmaceutical preparation or composition containing erythritol, but fail to describe intrabuccal dissolution type preparations.

This invention provides solid pharmaceutical preparations which can be readily administered even without water, especially solid pharmaceutical preparations which quickly disintegrate and dissolve in the oral cavity.

SUMMARY OF THE INVENTION

As a result of intensive studies and researches, the present inventors found that the preparations comprising the particular three ingredients, erythritol, crystalline cellulose and a disintegrant, in addition to a pharmaceutically active or medicinal ingredient, have characteristics of fast disintegrating and/or dissolving in the oral cavity, followed by further studies, which was led to completion of the present invention.

That is, this invention relates to (1) a solid pharmaceutical preparation comprising (i) a pharmaceutically active ingredient, (ii) erythritol, (iii) crystalline cellulose and (iv) a disintegrant; (2) the solid pharmaceutical preparation in (1), which is capable of buccal disintegration or dissolution; (3) the solid pharmaceutical preparation in (1), which further comprises mannitol; (4) the solid pharmaceutical preparation in (1), wherein the disintegrant is crospovidone; (5) the solid pharmaceutical preparation in (1), wherein erythritol is contained in a proportion of 5–90 parts by weight, based on 100 parts by weight of the solid pharmaceutical preparation; (6) the solid pharmaceutical preparation in (1), wherein the crystalline cellulose is contained in a proportion of 3–50 parts by weight, based on 100 parts by weight of the solid pharmaceutical preparation; (7) the solid pharmaceutical preparation in (1), wherein the disintegrant is contained in a proportion of 1–10 parts by weight, based on the solid pharmaceutical preparation; (8) the solid pharmaceutical preparation in (1), wherein the ingredients, (i) a pharmaceutically active ingredient, (ii) erythritol, (iii) crystalline cellulose and (iv) a disintegrant, are uniformly mixed, preferably throughout the preparation; (9) the solid pharmaceutical preparation in (1), which is a tablet; (10) a solid pharmaceutical preparation capable of buccal disintegration or dissolution, which comprises 0.3–50 parts by weight of (i) a pharmaceutically active ingredient, 50–80 parts by weight of (ii) erythritol, and 5–20 parts by weight of (iii) crystalline cellulose and 3–7 parts by weight of (iv) a disintegrant; (11) the solid pharmaceutical preparation in (1), wherein the pharmaceutically active ingredient is an antidinics or a drug for kinetosis or motion sickness; (12) a method of improving buccal disintegration or dissolution of a solid pharmaceutical preparation containing (i) a pharmaceutically active ingredient, which comprises incorporating (ii) erythritol, (iii) crystalline cellulose and (iv) a disintegrant in combination in the solid pharmaceutical preparation; (13) a method of making a solid pharmaceutical preparation, which comprises blending a mixture of (i) a pharmaceutically active ingredient, (ii) erythritol, (iii) crystalline cellulose and (iv) a disintegrant, and producing the solid pharmaceutical preparation from the mixture; (14) the method according to (13), wherein the solid preparation dissolves completely in solely buccal saliva within 1 minute of administration to a patient; and (15) a method of inhibiting or treating a disease of a subject in need thereof, which comprises administering to the subject an effective amount of (i) a pharmaceutically active ingredient for the disease as a solid pharmaceutical preparation containing (ii) erythritol, (iii) crystalline cellulose and (iv) a disintegrant in addition to the pharmaceutically active ingredient (i), with improved buccal disintegrability and/or dissolubility.

DETAILED DESCRIPTION OF THE INVENTION

The pharmaceutically active or medicinal ingredient to be used in the present invention may be in any optional form, for example, a solid, powder or granular, crystalline, oily or solution form.

There is no limitation to the pharmaceutically active ingredients to be used. As the pharmaceutically active ingredient, for example, there may be mentioned one or more members selected from the group consisting of nourishing and health-promoting agents, antipyretic-analgesic-antiinflammatory agents, antipsychotic drugs, antianxiety drugs, antidepressants, hypnotic-sedatives, spasmolytics, gastrointestinal function conditioning agents, antacids, antitussive-expectorants, dental buccal drugs, antihistamines, cardiotonics, antiarrhythmic drugs, diuretics, antihypertensive drugs, vasoconstrictors, coronary vasodilators, peripheral vasodilators, cholagogues, antibiotics, chemotherapeutic drugs, antidiabetic agents, drugs for osteoporosis, skeletal muscle relaxants, antidinics or drug for kinetosis or motion sickness and the like.

Examples of the nourishing and health-promoting agents include vitamins such as vitamin A and its derivatives, vitamin D and its derivatives, vitamin E and its derivatives (d-α-tocopherol acetate etc.), vitamin $B_1$ and its derivatives (dibenzoylthiamine, fursultiamine hydrochloride etc.), vitamin $B_2$ and its derivatives (riboflavin butyrate etc.), vitamin $B_6$ and its derivatives (pyridoxine hydrochloride etc.), vitamin C and its derivatives (ascorbic acid, sodium L-ascorbate etc.), vitamin $B_{12}$ and its derivatives (hydroxocobalamin acetate etc.), etc., as well as minerals such as calcium, magnesium and iron, proteins, amino acids, oligosaccharides, crude drugs and the like. Examples of the antipyretic-analgesic-antiinflammatory agents include, aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous caffeine, serratiopeptidase, lysozyme chloride, tolfenamic acid, mefenamic acid, diclofenac sodium, flufenamic acid, salicylamide, aminopyrine, ketoprofen, indomethacin, bucolome, pentazocine and so on.

Examples of the antipsychotic drugs include chlorpromazine, reserpine and so on. Examples of the antianxiety drugs include chlordiazepoxide, diazepam, etc. Examples of the antidepressants include imipramine, maprotiline, amphetamine and so on. Examples of the hypnotic-sedatives include estazolam, nitrazepam, diazepam, phenobarbital sodium and so on. Examples of the spasmolytics include scopolamine hydrobromide, diphenhydramine hydrochloride, papaverine hydrochloride and so on.

Examples of the gastrointestinal function conditioning agents include stomachic-digestives such as diastase, saccharated pepsin, scopolia extract, lipase AP, cinnamon oil, etc., intestinal function controlling drugs such as berberine chloride, resistant lactic acid bacterium, Lactobacillus bifidus and so on. Examples of the antacids include magnesium carbonate, sodium hydrogen carbonate, magnesium aluminometasilicate, synthetic hydrotalcite, precipitated calcium carbonate, magnesium oxide and so on.

Examples of the antitussive-expectorants include chloperastine hydrochloride, dextromethorphan hydrobromide, theophylline, potassium guaiacolsulfonate, guaifenesin etc. Examples of the dental buccal drugs include oxytetracycline, triamcinolone acetonide, chlorhexidine hydrochloride, lidocaine and so on.

Examples of the antihistamines include diphenhydramine hydrochloride, promethazine, isothipendyl hydrochloride, d1-chlorpheniramien maleate, etc. Examples of the cardiotonics include etilefrine hydrochloride and so on. Examples of the antiarryhythmic drugs include procainamide hydrochloride, propranolol hydrochloride, pindolol and so on. Examples of the diuretics include isosorbide, furosemide and so on. Examples of the antihypertensive drugs include delapril hydrochlororide, captopril, hexamethonium bromide, hydralazine hydrochloride, labetalol hydrochloride, methyldopa and the like.

Examples of the vasoconstrictors include phenylephrine hydrochloride, etc. Examples of the coronary vasodilators include carbocromen hydrochloride, molsidomine, verapamil hydrochloride and so on. Examples of the peripheral vasodilators include cinnarizine and so on. Examples of the cholagogues include dehydrocholic acid, trepibutone and so on.

Examples of the antibiotics include cephems, penems and carbapenems such as cefalexin, amoxicillin, pivmecillinam hydrochloride, cefotiam dihydrochloride etc. Examples of the chemotherapeutic drugs include sulfamethizole, thiazosulfone and so on. Examples of the antidiabetic agents include tolbutamide, voglibose and so on. Examples of the drugs for osteoporosis include ipriflavone and so on. Examples of the skeletal muscle relaxants include methocarbamol and so on. Examples of the antidinics or drugs for kinetosis or motion sickness, i.e. antimotion sickness drug, include meclizine hydrochloride, dimenphydrinate and so on.

The pharmaceutically active or medicinal ingredient may be diluted with a diluent which is used generally in the pharmaceutical or food industry. At least one of the pharmaceutically active ingredients may be in an oily form.

Among such pharmaceutically active ingredients, preferred examples for purposes of the present invention are vitamins, crude drugs, antipyretic-analgesic-antiinflammatory agents, antianxiety drugs, hypnotic-sedative agents, gastrointestinal function conditioning agents, antitussive-expectorants, antihypertensive drugs, antidiabetics, drugs for osteoporosis, skeletal muscle relaxants and antidinics or drugs for kinetosis or motion sickness.

Especially preferable active ingredients for the present invention are antidinics or drugs for kinetosis or motion sickness in that such drugs are often required to be administered without water for prevention or treatment of kinetosis or motion sickness.

The solid pharmaceutical preparations of the present invention contain the above-mentioned pharmaceutically active or medicinal ingredients usually in a proportion of about 0.05–70% by weight, preferably about 0.1–50% by weight, more preferably 0.3–30 % by weight.

Erythritol to be used as one of the raw materials for the preparations of the present invention is a kind of sugar alcohol and is in general produced by fermentation with yeasts using glucose as the starting material. Usually, erythritol products having a particle size capable of passing through a 50 mesh sieve are used. These products are available on the market, and examples of such products include erythritol manufactured by Nikken Chemical Co., Ltd.

Erythritol is incorporated in a proportion of about 5–90 parts by weight, preferably about 10–80 parts by weight, more preferably about 50–80 parts by weight, based on 100 parts by weight of the solid pharmaceutical preparation.

The preparation of the present invention preferably comprises crystalline cellulose, which is also called microcrystalline cellulose, and typically such crystalline cellulose that is produced by partially depolymerizing α-cellulose and purifying the resultant polymer can be used.

Examples of the crystalline cellulose to be used in the present invention include products of various grade such as CEOLUS KG801, avicel PH101, avicel PH102, avicel PH301, avicel PH302, avicel RC-591 (crystalline cellulose carmellose sodium) and so on. As the crystalline cellulose, one species may be used singly or alternatively two or more species may be used in combination. More preferred examples of the crystalline cellulose are CEOLUS KG801 which is called avicel of high compressibility. These raw materials are available on the market, which are exemplified by the products manufactured by Asahi Chemical Co., Ltd.

Crystalline cellulose is contained in a proportion of about 3–50 parts by weight, preferably about 5–40 parts by weight, more preferably about 5–20 parts by weight, based on 100 parts by weight of the solid pharmaceutical preparation.

As the disintegrants to be used for the present invention, unless the object of the invention is interfered with, any disintegrants which are in common use in the pharmaceutical filed. Examples of most preferred disintegrants include those known as super disintegrant such as crospovidone (ISP Inc., BASF), croscarmellose, croscarmellose sodium (FMC-Asahi Chemical Co., Ltd.), carmellose calcium [Gotoku Chemical (Yakuhin)]. Other preferred examples of disintegrants include carboxymethylstarch sodium (Matsutani Chemical Co., Ltd.), low substituted hydroxypropyl cellulose (Shin-Etsu Chemical Co., Ltd.), corn starch and so on. These disintegrants can be used singly or two or more species can be used in combination. For example, preferably, crospovidone may be used singly or in combination with other disintegrants. Here, as crospovidone, any cross-linked homopolymer called 1-ethenyl-2-pyrrolidinone homopolymer may be used, and usually crospovidone having a molecular weight of 1,000,000 or more. Specific examples of crospovidone available in the market include Cross-linked povidone, Kollidon CL, Polyplasdone XL, Polyplasdone XL-10, INF-10 (manufactured by ISP), polyvinylpolypyrrolidone, PVPP and 1-vinyl-2-pyrrolidinone homopolymer.

These disintegrants are usually incorporated in a proportion of about 1–15 parts by weight, preferably about 1–10 parts by weight, more preferably about 3–7 parts by weight, based on 100 parts by weight of the solid pharmaceutical preparation.

In the present invention, in addition to the above-mentioned ingredients, mannitol can be further added. Mannitol available on the market can be employed, and such mannitol is exemplified by the product manufactured by Towa Chemical (Kasei) Co., Ltd. Usually, mannitol is employed with a particle size capable of passing through a 150-mesh sieve.

The solid pharmaceutical preparations of the present invention are useful especially as buccal dissolution type solid preparations, which, though in a solid form, after orally administered, intrabuccally dissolve or disintegrate without being swallowed. As the dosage form of the solid preparations, there may be generally mentioned granules, tablets and the like. More preferable dosage forms of the solid preparations of the present invention are tablets. Such tablets are characterized in that they have appropriate hardness.

Unless the object of the invention is interfered with, the above-mentioned preparation of the present invention may further contain a variety of additives which are commonly employed in the manufacture of preparations in general dosage forms.

The additives mentioned above include, among others, binders, acids, foaming agents, artificial sweeteners, flavorants, lubricants, colorants and so on.

Examples of the binders include hydroxypropylcellulose, hydroxypropylmethylcellulose, α-starch, polyvinylpyrrolidone, gum arabic powder, gelatin, pullulan and the like.

Examples of the acids include citric acid, tartaric acid, and malic acid and so on. Examples of the foaming agents include sodium hydrogen carbonate and so on. Examples of the artificial sweeteners include saccharin sodium, dipotassium glycyrrhizinate, aspartame, stevia, thaumatin and so on. Examples of the flavorants include lemon, lemon lime, orange, menthol and the like. Examples of the lubricants include magnesium stearate, sucrose fatty acid ester, polyethyleneglycol, talc, stearic acid and the like. Examples of the colorants include various food colorants e.g. FD&C Yellow No. 5, FD&C RED No.2, FD&C Blue No.2, etc., food lakes, red iron oxide and so on.

Preferably, the solid pharmaceutical preparation of the present invention comprises the above-mentioned ingredients homogeneously or uniformly. In other words, the ingredients are preferably intimately and uniformly mixed throughout the preparation.

The solid pharmaceutical preparation according to the present invention may be produced in a conventional method and usually may be prepared by means of blending a mixture of (i) the pharmaceutically active ingredient and other ingredients, if necessary, followed by kneading, drying or molding. For tablets, further tabletting or compression-molding is carried out to give tablets.

The blending of the above pharmaceutically active or medicinal ingredients with the raw materials for the preparations in dosage forms can be carried out by any of the conventional blending techniques such as mixing, kneading and so on. Specifically, Vertical Granulator GV10 (manufactured by Powrex Corp.), Universal Kneader (manufactured by Hata Iron Works Co., Ltd.) and fluidized bed granulator FD-5S (manufactured by Powrex Corp.), for instance, can be employed.

The blend of the pharmaceutically active ingredients and the raw materials for the preparations in dosage forms may be directly tabletted, but it is usually subjected to kneading prior to tabletting.

The kneading operations of the blend containing water can be carried out by the routine method commonly used in the art. For example, the devices mentioned hereinbefore for the blending of the pharmaceutically active or medicinal ingredients with the other ingredients as the raw materials can be utilized. The drying operation can be carried out by any of the techniques used commonly in the art, such as vacuum drying, freeze-drying, spontaneous drying, fluidized-bed drying, and so on.

The tabletting or compression-molding for tablets can be carried out using an equipment commonly used in the granulation and compression-molding of tablets. For example, a single-punch tabletting machine (Kikusui Seisakusho) or a rotary type tabletting machine (Kikusui Seisakusho) can be employed. The molding pressure is generally about 0.5–3 ton/cm$^2$.

The solid pharmaceutical preparations, especially the buccal dissolution type tablets, of the present invention thus obtained have fast disintegrability and dissolubility in the oral cavity.

That is, the buccal dissolution time of the buccal dissolution type tablet of the present invention (the time for healthy male adults to complete dissolution by buccal saliva)

is usually about 0.1–1.0 minutes, preferably about 0.1–0.8 minutes, more preferably about 0.1–0.5 minutes. The hardness of each tablet (measured with a tablet hardness tester) is usually about 2–15 kg, preferably about 3–10 kg.

Therefore, the buccal dissolution type tablets of the present invention can be used for the therapy or prophylaxis of various diseases just as the conventional preparations containing the same pharmaceutically active ingredient but with an increased ease of administration or ingestion by aged persons and children, and also as safe preparations in case of emergency for general adults. The tablet of the invention further features a long shelf-life. The solid pharmaceutical preparation can be in general administered in the same manner as conventional preparations in dosage forms for oral administration and more easily even without water.

That is, the solid pharmaceutical preparation has low toxcity and is easy to take and therefore can be safely administered to humans ranging from children to aged people. While depending on the active ingredient, severity and age of the subject and so on, the dosage varies, the dosage is in general the same as the conventional preparations of the respective pharmaceutically active ingredients. For example, for the preparation of meclizine hydrochloride, the daily dosage for adult is about 1–100 mg, preferably about 10–75 mg as the active ingredient. Also, the daily dosage for adult of scopolamine hydrobromide is about 0.01–1 mg, preferably about 0.05–0.5 mg.

The following examples are further illustrative but by no means limitative of the present invention.

EXAMPLES

The physical properties of the tablets prepared in the Examples and Comparative Examples were determined by the following test methods.
(1) Hardness test
The hardness of each tablet was measured with a tablet hardness tester (manufactured by Schleuniger). The test was performed in 3–10 runs and the mean of the measurement results were shown.
(2) Buccal dissolution time
The time for a male adult to complete disintegration or dissolution only by saliva in the oral cavity was measured.

Examples 1–2 and Comparative Examples 1–3

The compositions of the preparations of Examples 1 and 2 of the present invention and those of Comparative Examples 1,2 and 3 are shown in Table 1.

A kneading machine (Powrex Vertical Granulator) was charged with medicinal ingredients, erythritol (manufactured by Nikken Chemical Co., Ltd.), mannitol (manufactured by Towa Chemical (Kasei) Co., Ltd.), crystalline cellulose (manufactured by Asahi Chemical Co., Ltd.) and crospovidone (polyplasdone XL-10, manufactured by ISP Inc.) in the respective amounts indicated in the formulas, and the charge was kneaded (at 400 rpm for 3 minutes) with a 50% ethanol solution. The kneaded mass was dried and comminuted with a powermill (with 1.5 mm screen). After addition of magnesium stearate in a proportion of 0.3%, the granules were compression-molded or tabletted using a rotary type tabletting machine (manufactured by Kikusui Seisakusho Co., Ltd.), with a punch having a beveled edge, 10 mm in diameter, at a molding pressure of 1.2 ton/cm$^2$, to provide tablets each weighing 400 mg. The hardness and buccal dissolution time of each tablet thus obtained was measured. The results are shown in Table 2.

TABLE 1

| Formula | Example 1 | Example 2 | Comparative Example 1 | Comparative Example 2 | Comparative Example 3 |
|---|---|---|---|---|---|
| Meclizine hydrochloride | 50 | 50 | 50 | 50 | 50 |
| Scopolamine hydrobromide | 0.25 | 0.25 | 0.25 | 0.25 | 0.25 |
| Caffeine | 40 | 40 | 40 | 40 | 40 |
| Vitamin B$_6$ | 20 | 20 | 20 | 20 | 20 |
| Erythritol | 529.75 | 264.8 | 344.9 | 284.8 | 284.8 |
| Mannitol | — | 264.95 | 344.85 | 284.95 | 284.95 |
| Low substituted hydroxypropyl-cellulose | — | — | — | — | 120 |
| Crystalline cellulose | 120 | 120 | — | 120 | — |
| Crospovidone | 40 | 40 | — | — | — |
| Total | 800.0 g | 800.0 g | 800.0 g | 800.0 g | 800.0 g |

TABLE 2

| Physical property | Example 1 | Example 2 | Comparative Example 1 | Comparative Example 2 | Comparative Example 3 |
|---|---|---|---|---|---|
| Hardness (kg) | 5.2 | 6.2 | 2.3 | 5.0 | 6.2 |
| Buccal dissolution time (second) | 18 | 25 | 115 | 92 | 140 |

Examples 3–4 and Comparative Example 4

In Table 3, the compositions are shown of the preparations of Examples 3 and 4 of the present invention and the preparation of Comparative Example 4 for comparison.

Medicinal ingredients, erythritol (manufactured by Nikken Chemical Co., Ltd.), mannitol (manufactured by Towa Kasei Co., Ltd.), crystalline cellulose (manufactured by Asahi Chemical Co., Ltd.), crospovidone (manufactured by ISP Inc.) and magnesium stearate 1.0% were blended in accordance with the respective formulas and tabletted by a dirtet tabletting method with a rotary type tabletting machine (manufactured by Kikusui Seisakusho Co., Ltd.) with a molding punch having a beveled edge, 10 mm in diameter, at a pressure 1.2 ton/cm$^2$, to provide tablets each weighing 400 mg. The hardness and buccal dissolution time of each tablet thus obtained was measured. The results are shown in Table 4.

TABLE 3

| Formula | Example 3 | Example 4 | Comparative Example 4 |
|---|---|---|---|
| Meclizine hydrochloride | 50 | 50 | 50 |
| Scopolamine hydrobromide | 0.25 | 0.25 | 0.25 |
| Caffeine | 40 | 40 | 40 |
| Vitamin B$_6$ | 20 | 20 | 20 |
| Erythritol | 204.90 | 204.90 | 204.90 |
| Mannitol | 204.85 | 204.85 | 204.85 |
| Low substituted hydroxypropylcellulose | — | — | 240 |
| Crystalline cellulose | 240 | 240 | — |
| Crospovidone | 40 | — | 40 |

TABLE 3-continued

| Formula | Example 3 | Example 4 | Comparative Example 4 |
|---|---|---|---|
| Croscarmellose sodium | — | 40 | — |
| Total | 800.0 g | 800.0 g | 800.0 g |

TABLE 4

| Physical property | Example 3 | Example 4 | Comparative Example 4 |
|---|---|---|---|
| Hardness (kg) | 6.6 | 5.1 | 6.8 |
| Buccal dissolution time (second) | 33 | 45 | 105 |

Example 5 and Comparative Example 5

In Table 5, there are shown the compositions of the preparations of Example 5 of the present invention and the preparation of Comparative Example 5 for comparison.

A fluidized-bed granulator (Powrex Co., Ltd. LAB1) was charged with the medicinal ingredients, erythritol (manufactured by Nikken Chemical Co., Ltd.), crystalline cellulose (manufactured by Asahi Chemical Co., Ltd.), crospovidone (manufactured by ISP Inc.), citric acid and aspartame, and granulation was carried out using water, wherein scopolamin hydrobromide was dissolved in 200 ml of water. After magnesium stearate (0.5%) was added to the resultant granules, the mixture was compression-molded with a rotary type tabletting machine (manufactured by Kikusui Seisakusho Co., Ltd.) a punch having a beveled edge, 10 mm in diameter, at a molding pressure of 0.8 ton/cm$^2$, to provide tablets each weighing 400 mg.

Measurement was carried out for hardness and buccal dissolution time of the obtained tablets. The results are shown in Table 6.

TABLE 5

| Formula | Example 5 | Comparative Example 5 |
|---|---|---|
| Meclizine hydrochloride | 31.25 | 31.25 |
| Scopolamine hydrobromide | 0.16 | 0.16 |
| Caffeine | 12.5 | 12.5 |
| Vitamin B$_6$ | 6.25 | 6.25 |
| Erythritol | 344.34 | 344.34 |
| Low substituted hydroxypropylcellulose | — | 75 |
| Crystalline cellulose | 75 | — |
| Crospovidone | 25 | 25 |
| Citric acid | 5.0 | 5.0 |
| Aspartame | 0.5 | 0.5 |
| Total | 500.0 g | 500.0 g |

TABLE 6

| Physical property | Example 5 | Comparative Example 5 |
|---|---|---|
| Hardness (kg) | 6.1 | 6.7 |
| Buccal dissolution time (second) | 28 | 85 |

Example 6

In Table 7, there is shown the composition of the preparation of Example 6 of the present invention.

A fluidized-bed granulator (Powrex Co., Ltd. LAB1) was charged with the medicinal ingredients, erythritol (manufactured by Nikken Chemical Co., Ltd.), crystalline cellulose (manufactured by Asahi Chemical Co., Ltd.), citric acid, aspartame and Yellow No. 5 aluminum lake, and granulation was carried out using water, wherein a solution of scopolamine hydrobromide in 200 ml of water was added by spraying. After crospovidone (manufactured by ISP Inc.), light anhydrous silicic acid, ρ-menthol and magnesium stearate (0.5%) were added to the resultant granules, the mixture was compression-molded with a rotary type tabletting machine (manufactured by Kikusui Seisakusho Co., Ltd.) with a punch having a beveled edge, 10 mm in diameter, at a molding pressure of 0.8 ton/cm$^2$, to provide tablets each weighing 400 mg.

Measurement was carried out for hardness and buccal dissolution time of the obtained tablets. The results are shown in Table 8.

TABLE 7

| Formula | Example 6 |
|---|---|
| Meclizine hydrochloride | 25.0 |
| Scopolamine hydrobromide | 0.25 |
| Erythritol | 640.0 |
| Crystalline cellulose | 80.55 |
| Crospovidone | 40 |
| Citric acid | 8.0 |
| Aspartame | 1.2 |
| Light anhydrous silicic acid | 1.0 |
| Magnesium stearate | 4.0 |
| Yellow No. 5 aluminum lake | q.s. |
| l-Menthol | q.s. |
| Total | 800.0 g |

TABLE 8

| Physical property | Example 6 |
|---|---|
| Hardness (kg) | 5.7 |
| Buccal dissolution time (second) | 23 |

The solid pharmaceutical preparations such as buccal dissolution type tablets of the present invention have excellent intrabuccal disintegrability or dissolubility, and therefore, they are easily administered and ingested. Further, since they have an appropriate strength, they are excellent in long shelf life or stability. Accordingly, the solid pharmaceutical preparations can be advantageously used for the prevention or treatment of diseases in patients, particularly aged or pediatric patients.

What is claimed is:

1. A solid pharmaceutical preparation which comprises (i) a pharmaceutically active ingredient, (ii) erythritol, (iii) crystalline cellulose and (iv) a disintegrant.

2. A solid pharmaceutical preparation capable of buccal disintegration or dissolution comprising the solid pharmaceutical preparation of claim 1.

3. A solid pharmaceutical preparation as claimed in claim 1, which further comprises mannitol.

4. A solid pharmaceutical preparation as claimed in claim 1, wherein erythritol is contained in a proportion of 5–90 parts by weight, based on 100 parts by weight of the solid pharmaceutical preparation.

5. A solid pharmaceutical preparation as claimed in claim 1, wherein the crystalline cellulose is contained in a proportion of 3–50 parts by weight, based on 100 parts by weight of the solid pharmaceutical preparation.

6. A solid pharmaceutical preparation as claimed in claim 1, wherein the disintegrant is contained in a proportion of 1–10 parts by weight, based on the solid pharmaceutical preparation.

7. A solid pharmaceutical preparation as claimed in claim 1, wherein the ingredients, (i) a pharmaceutically active ingredient, (ii) erythritol, (iii) crystalline cellulose and (iv) a disintegrant, are uniformly mixed.

8. A tablet comprising the solid pharmaceutical preparation as claimed in claim 1.

9. A solid pharmaceutical preparation capable of buccal disintegration or dissolution, which comprises 0.3–50 parts by weight of (i) pharmaceutically active ingredient, 50–80 parts by weight of (ii) erythritol, and 5–20 parts by weight of (iii) crystalline cellulose and 3–7 parts by weight of (iv) a disintegrant.

10. A solid pharmaceutical preparation as claimed in claim 1, wherein the pharmaceutically active ingredient is an antidinics or a drug for kinetosis or motion sickness.

11. A method of improving buccal disintegration or dissolution of a solid pharmaceutical preparation containing (i) a pharmaceutically active ingredient, which comprises incorporating (ii) erythritol, (iii) crystalline cellulose and (iv) a disintegrant into the solid pharmaceutical preparation.

12. A method of making a solid pharmaceutical preparation, which comprises:

blending a mixture of (i) a pharmaceutically active ingredient, (ii) erythritol, (iii) crystalline cellulose and (iv) a disintegrant, and producing the solid pharmaceutical preparation from the mixture.

13. The method according to claim 11, wherein the solid preparation dissolves completely in solely buccal saliva within 1 minute of administration to a patient.

14. A method of inhibiting or treating a disease of a subject in need thereof, which comprises administering to the subject an effective amount of (i) a pharmaceutically active ingredient for the disease as a solid pharmaceutical preparation containing (ii) erythritol, (iii) crystalline cellulose and (iv) a disintegrant in addition to the pharmaceutically active ingredient (i), with an improved buccal disintegrability and/or dissolubility.

15. The solid preparation as claimed in claim 1, wherein the disintegrant is selected from the group consisting of croscarmellose, croscarmellose sodium, carmellose calcium, carboxymethylstarch sodium, low substituted hydroxypropyl cellulose and corn starch.

16. The solid preparation as claimed in claim 9, wherein the disintegrant is selected from the group consisting of croscarmellose, croscarmellose sodium, carmellose calcium, carboxymethylstarch sodium, low substituted hydroxypropyl cellulose and corn starch.

* * * * *